United States Patent [19]

Frank et al.

[11] 4,259,313

[45] Mar. 31, 1981

[54] FLUORESCENT LABELS

[75] Inventors: David S. Frank, Rochester; Michael W. Sundberg, Penfield, both of N.Y.

[73] Assignee: Eastman Kodak Company, Rochester, N.Y.

[21] Appl. No.: 66,962

[22] Filed: Aug. 16, 1979

Related U.S. Application Data

[60] Division of Ser. No. 952,424, Oct. 18, 1978, which is a continuation-in-part of Ser. No. 865,274, Dec. 28, 1977, abandoned.

[51] Int. Cl.³ .................. G01N 31/00; G01N 31/22; G01N 33/48; G01N 33/00
[52] U.S. Cl. .................................. 424/8; 424/1; 424/7; 424/12; 424/16; 23/230 B
[58] Field of Search .............. 424/7, 8, 12, 1, 16; 23/230 B

[56] References Cited

U.S. PATENT DOCUMENTS

| | | | |
|---|---|---|---|
| 3,088,875 | 5/1963 | Fisk | 424/12 |
| 3,551,555 | 12/1970 | Schuurs | 424/12 |
| 3,553,310 | 1/1971 | Csizmas et al. | 424/2 |
| 3,853,987 | 12/1974 | Dreyer | 424/12 |
| 3,939,350 | 2/1976 | Krenick et al. | 250/365 |
| 4,020,151 | 4/1977 | Bolz et al. | 424/1.5 |
| 4,061,466 | 12/1977 | Sjohölm et al. | 23/230 B |
| 4,108,972 | 8/1978 | Dreyer | 424/1 |

FOREIGN PATENT DOCUMENTS 2628158 12/1976 Fed. Rep. of Germany .

OTHER PUBLICATIONS

Clin Chem. 23 (8), pp. 1492–1498, (1977).

Primary Examiner—Douglas W. Robinson
Attorney, Agent, or Firm—Arthur H. Rosenstein

[57] ABSTRACT

There are described stabilized fluorescent labels comprising rare earth chelate incorporated in polymeric beads derived from a latex. Labeled reactive proteinaceous species such as labeled immunoreagents comprising the stabilized fluorescent labels having protein absorbed or covalently bonded thereto are also described.

6 Claims, No Drawings

FLUORESCENT LABELS

This is a division of application Ser. No. 952,424, filed Oct. 18, 1975, which is a continuation-in-part of U.S. Application Ser. No. 865,274 filed Dec. 28, 1977 now abandoned.

BACKGROUND OF THE INVENTION

1. Field of the Invention

The present invention relates to fluorescent labels for various proteinaceous species and more particularly to fluorescent labels useful for the preparation of immunoreagents comprising fluorescently labeled antigens or antibodies.

2. Description of Related Art

Immunoassay is a field where sensitivity is of prime importance due to the low analyte levels that are measured. Radioimmunoassay sensitivity is limited to $10^{-12}$ M and is more often only in the $10^{-8}$ to $10^{-10}$ M range. In addition, radiolabels suffer from the drawbacks of short half life and handling hazards.

The sensitivity of fluorescence assays, although theoretically very high, is limited by the presence of background fluorescence. In many situations, it is impossible to reduce the background sufficiently (by appropriate filtration and other techniques known in the art) to obtain the desired sensitivity.

Time resolution offers an independent means of isolating the specific fluorescent signal of interest from nonspecific background fluorescence. This can be done if the label has much longer-lived fluorescence than the background, and if the system is illuminated by an intermittent light source such that the long-lived label can be measured during the dark period subsequent to the decay of the short-lived background. Such techniques are described in greater detail in German Offenlegungschrift No. 2,628,158 published Dec. 30, 1976.

The long-lived fluorescence (0.1–5 msec) of the aromatic diketone chelates of certain rare earth metals, for example, europiumbenzoylacetonate and europiumbenzoyltrifluoracetonate, has been known for some time. The chelating agent absorbs light and transfers it to the metal ion, which fluoresces. German OLS No. 2,628,158 describes the use of time resolution in fluorometric immunoassays (FIA) through the use of fluorescent labels whose emissions are long lived as compared to those of species which produce background interferences in such assays. This publication also provides a useful discussion of the techniques of FIA and its advantage over other immunoassay techniques such as radioimmunoassay (RIA).

The fluorescent immunoreagents described in German OLS No. 2,628,158 comprise at least one member of the immune-complement system, i.e., an antibody or an antigen, "conjugated" with a rare earth chelate. Such "conjugation" can be achieved in one of two ways:

(1) by first labeling, i.e., attaching the rare earth chelate to the antigen as described in "Fluorescent Antibody Techniques and Their Application" by A. Kawamura, Ed., University Park Press, Baltimore, Maryland, 1969, and then adding antibody to the conjugated antigen whereby the antibody and antigen join in the usual fashion, or:

(2) by covalent bonding of the antibody to the chelate via a chemical group which binds to both antibodies and the chelates.

The problem with immunoreagents of the type described in German OLS No. 2,628,158 is that the fluorescent labeling species, namely the rare-earth chelates, are quenched, i.e., their fluorescence is extinguished, when contacted with water. This problem, hereinafter referred to as an "aqueous stability" problem, is particularly serious because a principal use for fluorescent labeled immunoreagents is in the assay of aqueous biological liquids such as blood, serum, etc. If aqueous stability could be conferred on these materials, they would be useful as fluorescent labels for these biological liquids, thus allowing increased fluorescence immunoassay sensitivity by the use of time resolution of signal from background.

Belgian Patent Publication No. 843,647 published Dec. 30, 1976, describes scintillation counting compositions comprising polymeric particles derived from a latex and loaded with at least one hydrophobic fluor as well as methods for preparing such latices.

Leif, R. C. et al, Clinical Chemistry, Vol. 23, No. 8 (1977) suggest techniques for stabilizing rare earth chelates for use in aqueous liquids. The method generally comprises attaching a chelating agent to the surface of a polymeric bead and then chelating several other chelating agents and the bead-attached chelating agent to a single rare earth atom.

U.S. Pat. No. 3,853,987 issued Sept. 1, 1971, suggests the incorporation of "tracer" molecules throughout the volume of particles of acrylic acid derivatives in a latex and use of such particles as labels for immunoreagents. Although this patent teaches that the tracer is incorporated throughout the particle volume, there is no teaching of how the "tracer", fluorescent or radioactive, is incorporated into the particle. The only teachings are to attaching such "tracers" to acrylic polymers or adhering the "tracers" to the surface of such polymers.

SUMMARY OF THE INVENTION

It has now been discovered that the incorporation of long-lived fluorescent materials, especially rare earth chelates, into polymeric bead latices eliminates the fluorescent quenching of these fluorescent rare earth chelates by aqueous liquids. Accordingly, the present invention provides a class of highly efficient, aqueus stabilized fluorescent labels for proteinaceous species, especially antigen and antibody immunological species. The present invention also provides a new class of proteinaceous reagents, especially immunological reagents, bearing these highly useful fluorescent labels.

Thus, this invention describes long-lived fluorescent compositions prepared by incorporating chelates of the rare earth metals, preferably europium and terbium, into latex particles. The chelating agent strongly absorbs light and efficiently transfers energy to the metal. The latex configuration confers aqueous stability to fluorescent rare earth chelates which in the past have been subject to quenching in aqueous liquids. The polymeric beads derived from the latex and having the rare earth chelate incorporated therein can then be used as fluorescent labels to form labeled reagents by adsorbing or covalently binding antigens, antibodies, plant lectins, carbohydrates or other such proteinaceous compounds to the surface of the polymeric latex beads.

The use of these long-lived fluorescent labels makes it possible to take advantage of time resolution as a method of reducing background in, for example, fluorescence immunoassay systems as the particles do not prematurely precipitate. Furthermore, when the fluorescent rare earth chelate is incorporated into the latex bead according to the technique described in aforementioned Belgian Pat. No. 843,647, high levels of fluorescent rare earth chelates can be associated with antigen or antibody attached to the surface of the bead thereby producing an immunoreagent which demonstrates the reactivity of a single immunological unit, i.e., a single antigen or antibody, having a large quantity of label attached thereto, thus even further increasing the efficiency of the fluorometric immunoassay.

DESCRIPTION OF THE PREFERRED EMBODIMENTS

When used herein in reference to fluorescent rare earth chelates, the term "stabilized" means that the fluorescence of the chelate is not quenched when the label is immersed in or otherwise exposed to an aqueous medium.

Generally, any rare earth chelate which demonstrates fluorescent behavior is a candidate for use in the compositions described herein. A detailed discussion of such materials can be found in Chapter 8 of Sinha, Shiama P., Complexes of Rare Earths, Pergamon Press, 1966. The following references also provide an extensive discussion of rare earth chelates of the type useful in the compositions of the instant invention: Lytle, F. E., Applied Spectroscopy, 24:319 (1970) and Filipescu, N., et al, J. Phys. Chem., 68:3324 (1964).

The fluorescent compositions are comprised of chelates of the rare earth elements, preferably europium and terbium. Useful chelating agents for such rare earth elements have been discussed extensively in the literature referenced above and include by way of non-limiting examples: 1,3-diketones such as acetylacetonate, benzoylacetonate, benzoylbenzoate, trifluoro-2-furylacetylacetone; phthalates and naphthalates such as dinaphthoylmethide; dipyridines and terpyridines such as 2,2'-bypyridine-1,1'-dioxide, 2,2',6',2"-terpyridine, 4,4'-dimethyl-2,2'-dipyridine; and phenanthrolines such as o-phenanthroline isothiocyanate and the like.

The 1,3-diketones are preferred for use herein because of their high transfer efficiency.

To enhance the fluorescent yield of such chelates it may be desirable and it is preferred herein to include in the stabilized label beads small amounts of Lewis bases as described by Kleinerman, et al, J. Chem. Phys., 41:4009 (1964) and Halverson et al, J. Chem. Phys., 41:157 (1964). Trioctylphosphine oxide (TOPO) is a preferred Lewis base, although any of the other fluorescence enhancing materials described in the aforementioned Kleinerman and Halverson publications are similarly useful and may be preferred in certain environments of use.

The latices of the present invention are preferably, though not necessarily, prepared using the materials and methods described in aforementioned Belgian Pat. No. 843,647. The method described in this patent publication generally involves gradually increasing the hydrophilicity of a solution of a hydrophobe in a water-miscible solvent in the presence of uncoagulated, undissolved, loadable polymeric latex particles to a point at which substantially no hydrophobe remains dissolved in the water-miscible solvent phase. The increase in hydrophilicity is accomplished by adding water to the solution of hydrophobe in the water-miscible solvent. The advantage of imbibing the chelates using this technique is that substantially high concentrations of the fluorescent rare earth chelates up to about 7.5% by weight of the polymeric bead can be incorporated into the bead.

Further loading is achieved, and completed, by evaporation of the water-miscible solvent.

Water-Miscible Organic Solvents

The preferred water-miscible organic solvents are those which:

(a) can be dissolved in (i.e., are "miscible" with) distilled water at 20° C. to the extent of at least about 20 parts by volume of solvent in 80 parts by volume of water;

(b) have boiling points (at atmospheric pressure) above about 20° C.;

(c) do not detrimentally react chemically with the loadable polymer latexes which are useful in the practice of this invention;

(d) do not dissolve more than about 5 weight percent of such loadable polymer latices at 20° C.; and (e) act as solvents for the fluorescent rare earth chelates described hereinafter.

Examples of water-miscible solvents useful in the successful practice of the present invention include, solely by way of example, tetrahydrofuran, ethanol, methanol, acetone, and the like.

Loadable Polymeric Latices

Loadable polymer latices are herein defined as those which include any polymeric latex which (i) has a polymeric discontinuous phase (particles) which consists essentially of polymer polymerized from one or more ethenic monomers, from about 0 to about 10 weight percent of the polymer preferably being made from monomer containing a sulfonic acid or a sulfonate group, (ii) has an aqueous continuous phase, and (iii) does not coagulate or settle out when subjected to the following test:

Loadable Polymer Latex Test

At 25° C., slowly stir 250 ml of polymeric latex containing from about 10 to about 20 weight percent dispersed phase into an equal volume of acetone. The addition should take place over 1 minutes at a steady, uniform rate, while the acetone is being stirred moderately. Discontinue the agitation and let the resulting blend stand at about 25° C. for 10 minutes. At the end of that time observe the blend. "Loadable polymer latices" are those which exhibit essentially no visible coagulation or settling out under these test conditions.

Preferred Loadable Polymeric Latices

Although any polymeric latex which will meet conditions (i)–(iii) above is useful, polymeric latices which are particularly useful in the successful practice of the present invention are those loadable latices wherein the discontinuous phase comprises a polymer made of (a) from about 0 to about 100 weight percent of a styrene monomer having the formula

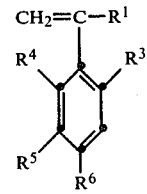

wherein $R^1$ is hydrogen or methyl; $R^3$ and $R^4$ are hydrogen or lower alkyl of 1 to about 4 carbon atoms; $R^5$ and $R^6$ are substituted vinyl or sulfonyl, for example haloalkylcarbonyl, vinylsulfonyl, etc.; hydrogen, or lower alkyl of 1 to about 4 carbon atoms which can be substituted in the alpha position, for example halogen, alkyl sulfonyl halide, etc. or $R^5$ with $R^4$ can constitute the atoms necessary to complete a fused benzene ring;

of which particularly useful examples are styrene, vinyltoluene, 2-vinylmesitylene, chloroethylsulfonyl methyl styrene, and 1-vinylnaphthalene; and either or both of (b) from about 0 to about 95 weight percent of units derived from one or more ethenic monomers of the formula

wherein R is hydrogen or alkyl containing 1 to about 5 carbon atoms; $R^1$ is hydrogen or methyl; and $R^2$ is hydrogen, halogen, methyl, cyano, the group

or the ester

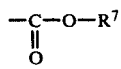

wherein $R^{10}$ is H or $R^7$, $R^7$ is an aliphatic group containing from 1 to about 6 carbon atoms and can be unsubstituted or substituted with an amine group which can be further substituted to a quaternary ammonium group; and (c) from about 0 to about 10 weight percent of a hydrophilic ethenic monomer containing a sulfonic acid group, or an ammonium or alkali metal salt thereof; said ethenic monomer preferably having a molecular weight of at most about 300. In addition, other monomers of the class (a), (b), or (c), can be added, where copolymerization is possible, provided that at least one of (a) (b) and (c) are present. A monomer such as acrylamide can be used where additional hydrophilicity is required to improve the stability of the latex.

It should be noted that the ratios of monomers set out herein are based upon the relative proportions of various monomers as they are charged into the polymerization reactor in a conventional free radical polymerization process. Products from such reactions may vary to some extent in the ratios derived from the charged monomers for various reasons which are well known to those skilled in the art of manufacturing synthetic polymeric latices. While "loadable" polymer latices can be made from one, two, three, four, or even more different monomers, those which are preferred for use in the practice of this invention are generally comprised of two to four different types of monomers, depending upon the particular properties desired in the final products of the invention. As the manufacture of latices of this type is well known, details of such procedures need not be described herein, except to point out that the preferred "loadable" polymer latices described above are generally prepared via free radical initiated reactions of monomers dispersed in an aqueous medium with one or more appropriate surfactants. See, for example, U.S. Pat. Nos. 2,914,499; 3,033,833; 3,547,899; and Canadian Pat. No. 704,778.

Polymers which are still further preferred for use as loadable polymeric latices are those wherein (1) the acrylic monomer of the formula

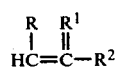

is acrylonitrile or an ester selected from the group consisting of methyl, ethyl, propyl and n-butyl acrylates and methacrylates, and (ii) the hydrophilic ethenic monomer, if used, is selected from those having a sulfonic acid group (or water soluble salt thereof) preferably attached to a terminal carbon atom such as, for example, those having the following structure:

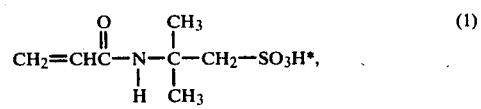 (1)

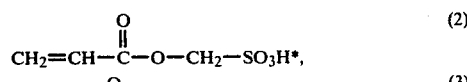 (2)

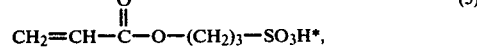 (3)

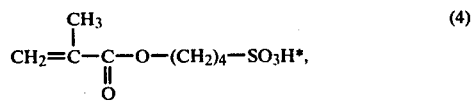 (4)

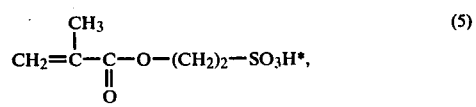 (5)

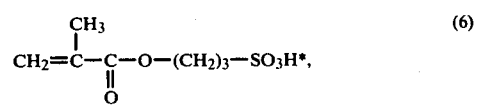 (6)

 (7)

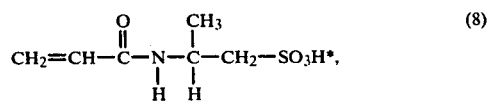 (8)

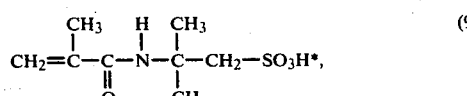 (9)

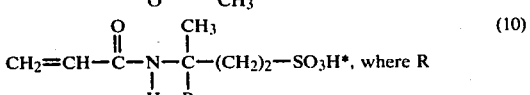 (10)

where R is H or $CH_3$.

(* = in place of H can be an alkali metal cation, preferably $Na^+$ or $K^+$, or ammonium ion.)

The generic formula for a preferred subclass of hydrophilic ethenic monomers containing the sulfonic acid group is

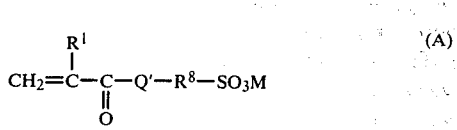

where $R^1$ is methyl or hydrogen; $R^8$ is a straight or branched chain alkylene group containing 1 to 5 carbon atoms such as methylene, ethylene, 2-methylethylene, trimethylene, tetramethylene or 2,2-dimethylethylene, 3-methyl propylene, 3,2-dibutylene, 2-methyl propylene and the like; M is ammonium, hydrogen, or alkali metal cation, and Q' is O or NH. Highly preferred bead compositions include:

(1) Poly(n-butyl acrylate-co-styrene-co-2-acrylamido-2-methylpropanesulfonic acid) (30:65:5)
(2) Poly(n-butyl acrylate-co-2-acrylamido-2-methylpropanesulfonic acid) (90:10)
(3) Poly[styrene-co(2-chloroethylsulfonylmethyl)styrene-co-2-acrylamido-2-methylpropanesulfonic acid] (88:7:5)
(4) Poly[styrene-co-acrylamide-co-(2-chloroethylsulfonylmethyl)styrene-co-2-acrylamido-2-methylpropanesulfonic acid] (75:14:6:5)
(5) Poly(n-butyl acrylate-co-styrene-co-m+p-chloromethylstyrene-co-2-acrylamido-2-methylpropanesulfonic acid) (33:30:35:2);
(6) Poly[n-butyl acrylate-co-styrene-co-m+p-chloromethylstyrene-co-2-(methacryloyloxy)ethyl-trimethylammonium methosulfate] (35:50:10:5); and
(7) Poly[styrene-co-acrylamide-co-(2-chloroethylsulfonylmethyl)styrene] (10:25:5)

From the foregoing description it is evident that many combinations of monomers can be used in the manufacture of synthetic polymeric latices in accordance with the most preferred embodiments of this invention. It must be pointed out, however, that many polymeric latices are not "loadable latices" as set out above. For this reason, it is recommended that, before a given latex is assumed to be "loadable", the latex be tested via the procedure set out above under the heading "Loadable Polymer Latex Test." The use of this test is also recommended as a control procedure because of the relatively low level of batch-to-batch reproducibility that sometimes occurs in the commercial manufacture of polymeric latices. A preferred method for manufacturing loadable latices is described below, preceding the Examples.

The dispersed polymeric particles comprising the discontinuous phase of the latex, formed in the manner described above, have an average diameter of from about 0.01 to about 0.2 micron. Thus, the latex can be considered a colloidal dispersion. Furthermore, a preferred concentration range of latex particles is such that the polymer portion thereof, calculated apart from the fluorescent rare earth chelate, gives a concentration of from about 0.03 g/cc to about 0.25 g/cc.

The concentration of fluorescent rare earth chelate in the bead will also vary to some extent depending upon the particular utility for which the bead is intended. Thus, an individual bead may contain at a minimum a single fluorescent rare earth chelate and as a maximum about 7.5% by weight. The use of chelate concentration levels at the high end of this range makes possible the detection of analyte at levels as low as $10^{-14}$–$10^{-15}$ M. A molar ratio of 1 metal: 3 chelating agent: 2 Lewis base is a preferred embodiment. The bead size can be chosen on the specific purpose for which the fluorescent label is intended; however, 0.01 to 0.15 μm diameter beads are preferred for most immunoassays.

Preferred Process of Manufacture of the Latex

With respect to the preferred process of manufacturing the compositions of the present invention, the order of addition of the loadable polymeric latex into the solution of fluorescent rare earth chelate dissolved in water-miscible solvent is important. Reversing the order results in the coagulation and settling out of the latex or the accumulation of a large proportion of the fluorescent rare earth chelate outside the latex particles in a much less desirable or less useful form.

In the manufacture of the loaded latex compositions employed in the practice of this invention, generally the relative volume of (a) loadable polymeric latex; and
(b) solution of fluorescent rare earth chelate(s)

(in water-miscible solvent) which are intermixed in the required manner, are not believed critical. Thus, so long as some loadable latex particles are present in the solution during that interval of time in which the fluorescent rare earth chelate is forced out of solution (because of the increasing hydrophilicity of the solution, as described above), some loaded polymeric latex particles will be created. For example, one embodiment of the present generic process involves, stepwise, (a) the introduction of a quantity of loadable polymeric latex which is not sufficient to affect the hydrophilicity of the solution of fluorescent rare earth chelate to the extent necessary to force the fluorescent rare earth chelate out of solution; and
(b) adding enough water to the resulting mixture to effect the desired transfer of fluorescent rare earth chelate from the water-miscible solvent into the latex particles.

In this way, loaded latex compositions containing relatively larger proportions of fluorescent rare earth chelate per particle can be made using a relatively dilute solution of fluorescent rare earth chelate. Thus, it can be seen that there is more than one technique whereby the necessary increase in the hydrophilicity of the solution of fluorescent rare earth chelate (during the period in which it becomes insoluble in such solution) can be obtained. For this reason, when the phrase "at least sufficient water to cause the fluorescent rare earth chelate to become insoluble in the solution" (with reference to the essential step of this process) is used herein, the "water" referred to in that phrase means not only water alone, but also the "aqueous" portion of a loadable aqueous polymeric latex as described hereinbefore, as well as water in the form of a solution of one or more dissolved salts and the like.

However, it is generally preferred that when the dispersed phase polymer "solids" of the loadable polymeric latex is above 10 weight percent, the relative amount of fluorescent rare earth chelate solution that is blended with such latex should be between about 50 and about 200 parts by volume per 100 parts by volume of loadable polymeric latex; and still more preferably, about one part by volume of fluorescent rare earth chelate solution per part by volume of loadable polymeric latex; particularly when the latex contains from about 12 to about 20 weight percent of polymeric particles. The actual optimum amount of time necessary to carry out the gradual mixing of (i) the latex and (ii) the fluorescent rare earth chelate solution in accordance with the present process will vary in any given instance, depending upon such factors as
(a) the identity of the polymeric latex, fluorescent rare earth chelate, and water-miscible solvent;
(b) the relative concentrations of fluorescent rare earth chelate and polymeric dispersed phase in the respective materials to be mixed, as well as;
(c) the relative amounts of latex and fluorescent rare earth chelate solution.

However, it is generally preferred that the gradual intermixing of loadable polymeric latex into the fluorescent rare earth chelate solution take place over at least about 10 seconds, particularly in those instances in which the polymeric "solids" content of the loadable polymeric latex is above about 12 weight percent. Too fast intermixing has been found to result in formation of a second solid phase in the system and/or coagulation or settling of the polymeric latex particles. Gradual intermixing over at least about 20 seconds is still further preferred.

Generally, after a useful loaded polymeric latex composition, as described, hereinbefore, has been formed initially, some or all of the water-miscible organic solvent can optionally be removed from the composition without harming the valuable utility of such loaded latex composition. Removal of water-miscible organic solvent can preferably be accomplished by evaporation under any of a wide variety of conditions (at temperatures below about 40° C., for example), preferably under reduced pressure. Preferably at least about half of the water-miscible solvent is removed from the initial compatible blend (of loadable polymeric latex/fluorescent rare earth chelate/water-miscible solvent) to thereby form one of the preferred useful loaded latex compositions of the present invention. Such preferred useful loaded latex compositions retain their "latex" characteristics; that is, they have an aqueous continuous phase which optionally contains some of the water-miscible organic solvent (but preferably not more water-miscible solvent than about 30 weight percent of said continuous phase), and a dispersed phase comprising loaded polymeric latex particles in which the fluorescent rare earth chelate is uniformly distributed. Removal of the organic solvent and/or some water from the initial blend of latex plus water-miscible solvent, of course, results in a composition having a higher "solids" content.

When it is desired to improve the stability of a loaded latex composition to inhibit the tendency of the latex to settle out gradually upon prolonged storage, the composition can be intermixed with an aqueous solution of a hydrophilic colloid such as gelatin. Such an embodiment is specifically preferred. A preferred minimum amount of hydrophilic colloid and/or a starch such as grafted starch in the resulting mixtures is about 1 weight percent based on the weight of the loaded latex composition, although more hydrophilic colloid can be used, if desired, to form a stabilized latex product.

The following is an illustrative, non-limiting example of the preparation of poly(n-butyl methacrylate-co-styrene-co-2-acrylamido-2-methylpropane sulfonic acid in a charge weight ratio of 50:40:10, which provides suitable "loadable" polymeric particles as described above:

To a one-liter addition flask were added 200 g of n-butyl methacrylate, 160 g of styrene, and a solution consisting of 7.7 g of NaOH, 350 ml H$_2$O, 40 g of 2-acrylamido-2-methylpropane sulfonic acid, and 2 g of "Triton 770" (40%) which is an anionic sodium salt surfactant of an alkylaryl polyether sulfate in liquid form manufactured by Rohm and Haas. The mixture was stirred for 30 min. prior to the addition process. In a 250 ml addition funnel was added 200 ml H$_2$O containing 2 g of K$_2$S$_2$O$_8$. Both the addition flask and the addition funnel were connected to a 3 liter reaction flask containing 800 ml H$_2$O and 4 g of "Triton 770" (40%) maintained at 95° C. with stirring. To start the polymerization, 1.2 g of Na$_2$S$_2$O$_5$ was added to the reaction flask immediately followed by the addition of monomer mixture and K$_2$S$_2$O$_8$ solution. The period of addition was about 30 min. The polymerization was allowed to proceed for an additional 30 min. The latex was then cooled and dialyzed overnight to give a solids content of 13.8%.

Loading of the latex with fluor is accomplished as described hereinbelow. The polymeric latex beads can then be used to label a variety of proteinaceous species by binding the protein to the surface of the bead either by adsorption or by covalent bonding. Among the proteinaceous species which can be labeled in this fashion are enzymes, antigens, antibodies, plant lecithins and similar such compositions.

Techniques for performing such binding of proteins to the surface of polymeric beads are well known in the art and an extensive quantity of patent and technical literature is directed to such techniques and specific linking groups for performing the attachment. German OLS No. 2,548,427 describes useful such techniques. Examples 1 and 2 below demonstrate useful adsorption and covalent bonding techniques according to the practice of the present invention.

When covalent bonding of the proteinaceous species to the polymer bead is desired, it is preferred to use for the latex bead a monomer which, after bead formation, retains a chlorobenzyl, chloroacetyl, chloroethylcarbonyl, chloroethylsulfonyl, acryloyl, or vinyl-sulfonyl group which can react with amino, amido, or sulfonamido groups on the enzyme, antibody, antigen, proteinaceous species or carbohydrates to be bound to the bead.

Accordingly, following attachment of the proteinaceous species, highly preferred fluorescent labeled polymers for use as the polymer latex of the bead are those having the following structural formula,

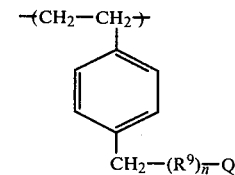

wherein Q is the proteinaceous species, n is 0 or 1, and R$^9$ is a linking group selected from the group consisting of (a) —SO$_2$CH$_2$CH$_2$—

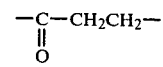

Other representative techniques for accomplishing binding are described in the following patents: U.S. Pat. Nos. 3,088,875; 3,766,013; 3,619,371; 3,809,613; 3,853,987; 3,963,441; 3,551,555; and 3,649,346. All of the aforementioned patents describe techniques for adsorbing or covalently bonding proteinaceous species, especially antigens and antibodies, to a variety of polymeric species of the type which are useful in the polymeric latex beads of the present invention. To the extent that these patents teach such methods they are incorporated herein by reference.

Once prepared as described hereinabove, the fluorescent latex bead labeled immunologically reactive species can be used in fluorescent immunoassays, particularly those which utilize temporal resolution of the specific detecting signal to distinguish from background as described in aforementioned German OLS No. 2,628,158. In this time-resolved mode (i.e. temporal resolution), the sample is excited in an intermittent fashion and information is accepted only during the dark cycle when the long-lived fluorescent label is still emitting strongly but when other sources of fluorescence have decayed. Discontinuous excitation can be achieved in a variety of ways, including pulsed laser, mechanical chopping of a continuous excitation beam, moving the sample in and out of the excitation beam, etc. Moreover, discontinuous excitation has the advantage of allowing the use of high radiant power without the absorption of a large amount of energy by the sample, thus diminishing the probability of sample photodegradation.

Typical such fluorescent radioimmunoassay techniques wherein the immunoreagents described herein find utility are described in U.S. Pat. Nos. 4,020,151; 3,939,350; and 3,901,654.

The following non-limiting examples will serve to better illustrate the successful practice of the instant invention:

In all of the examples, the europium complex that is imbibed into the latex is europium (III) (thenoyltrifluoroacetone)$_3$ along with trioctylphosphine oxide (TOPO) in the ratio of 1 Eu complex:2 TOPO. This is done according to the method of Belgian Pat. No. 843,647.

EXAMPLE 1

The Adsorption of Bovine Gamma Globulin to Latex Beads

Bovine gamma globulin (BGG) (50 mg) is dissolved in 100 ml of distilled water. To it is added 250 $\mu$l of a 7% suspension of europium-imbibed latex, poly(n-butyl acrylate-co-styrene-co-2-acrylamido-2-methylpropanesulfonic acid) (30:65:5), and the pH adjusted to 9.0 using a carbonate buffer. The mixture is chromatographed through BioGel A-5 (available from Bio Rad, Richmond, Calif.) resin (50 ml, 100–200 mesh) and eluted with water. The latex is filtered through a 0.22 $\mu$m Millipore® filter before use, and can be specifically precipitated with an antibody that reacts with BGG.

EXAMPLE 2

Covalent Attachment of Antigen to Fluoroescent Latex Beads

A. Binding BGG to Europium-Imbibed Latex

BGG (100 mg) is dissolved in 200 ml distilled water with stirring. Next, the pH is added to 9.6 with 6 N sodium hydroxide, and the solution cooled to 11° C. in a water bath shaker. 0.5 ml of a 7% suspension of europium-imbibed latex, poly[styrene-co-(2-chloroethylsulfonylmethyl)styrene-co-2-acrylamido-2-methylpropanesulfonic acid] (88:7:5), is added, and the reaction mixture shaken for 72 hours at 11° C. To this is added 0.1 ml ethanolamine, and the mixture is shaken an additional 24 hours at 11° C. The mixture is dialyzed against running distilled water for 72 hours. After dialysis, the dialyzate is chromatographed two times through BioGel A-5 resin (50 ml, 100–200 mesh) and eluted with water each time. A yield of 87.5 mg is obtained after lyophilization.

B. Binding of L-Thyroxine to Europium-Latex

L-thyroxine (0.15 g) is dissolved in 60 ml of stirred distilled water at pH 12 (adjusted with 6 N sodium hydroxide). Nine ml of a 7% suspension of 0.05 $\mu$m diameter europium-imbibed latex, poly[styrene-co-(2-chloroethylsulfonylmethyl)styrene-co-2-acrylamido-2-methylpropanesulfonic acid](88:7:5), is added, and the pH of the reaction mixture readjusted to 12 with 6 N sodium hydroxide. The reaction mixture is shaken for 4 days at 11° C. Butylamine (0.5 ml) is added and shaking is continued for 24 hours. The reaction mixture is dialzed against running ditilled water for 3 days and then against 4 liters of 1% aqueous bovine serum albumin for an additional 3 days. The dialyzed reaction mixture is slowly passed twice through 50 ml of BioGel A-5 resin. The eluate is passed through a sintered glass funnel (coarse grade) then dialyzed against running distilled water for 4 days and freeze-dried. The product weighs 0.5 g. Iodine calc. 20.5% (complete reaction of polymer); found.3.8%.

C. Binding of L-Thyroxine-Rabbit Gamma Globulin to Europium-Imbibed Latex

Part 1. Preparation of L-thyroxine-rabbit gamma globulin: In 200 ml of stirred distilled water 0.5 g ($3.3\times10^{-6}$ mole) rabbit gamma globulin is dissolved. 0.3 g ($7.1\times10^{-4}$ mole) of 1-cyclohexyl-3-(2-morpholinoethyl)-carbodiimide metho-p-toluenesulfonate is added to the stirred solution.

0.4 g ($5.2\times10^{-4}$ mole) of L-thyroxine is dissolved in 120 ml of N,N-dimethylformamide. The pH of the solution is adjusted to 6.5 (with dilute hydrochloric acid), and this solution added slowly to the stirred protein solution over a period of 20 min. Upon completion of the addition, an additional 0.4 g of the carbodiimide is added, and the reaction mixture stirred overnight at room temperature. The reaction mixture is dialyzed against running distilled water for 4 days then against 4 liters of 1% aqueous bovine serum albumin for 3 days. The dialyzate is freeze-dried. It weighs 0.53 g. Spectrophotometric analysis for L-thyroxine content indicated a ratio of 14 L-thyroxine units per rabbit gamma globulin. Iodine calculated on 14 units, 4.4%; found, 4.7%.

Part 2. Binding of L-thyroxine-rabbit gamma globulin to europium-imbibed latex: L-thyroxine-rabbit gamma globulin (0.1 g) prepared as described above was dissolved in 200 ml of distilled water. The pH is adjusted to 9.5 with 6 N sodium hydroxide and 0.5 ml of a 7% suspension europium-imbibed latex, poly[styrene-co-(2-chloroethylsulfonylmethyl)styrene-co-2-acrylamido-2-methylpropanesulfonic acid] (88:7:5), is added. The reaction mixture is shaken for 3 days at 11° C. Ethanolamine (0.1 ml) is added, and shaking continued for 24 hours. The reaction mixture is dialyzed against running distilled water for 48 hours then chromatographed twice on 50 ml of BioGel A-5 resin. The final volume of liquid is approximately 200 ml (0.2 mg/dl solids). Iodine percentage calculated for 78 $T_4$(L-thyroxine)-RGG/latex, 1.4%; found 0.88%. $T_4$-RGG/latex=40.

EXAMPLE 3

Specific Binding of the Fluorescent Latex Labeled Antigen to Antibody

A. Agglutination of the Latex-Bound Antigen by Antiserum

Ten microliters of a 0.02% suspension of 0.1 μm diameter europium-imbibed latex beads to which bovine gamma globulin was covalently bound were incubated in snap cap plastic tubes with 25 μl of rabbit antiserum to bovine gamma globulin in a total volume of 145 μl (phosphate-buffered saline, pH 7.5). After several hours, a precipitate was observed which was fluorescent when illuminated with light at 365 nm. In a parallel test with nonimmune rabbit serum, there was no precipitate.

B. Specific Binding of Antigen-coated Fluorescent Latex Beads to Antibody-Coated Micrometer Size Beads Test solutions are prepared in 1.5 ml snap cap plastic tubes containing the following:

1. 100 μl 3% Triton X-100 (Rohm and Haas) in 0.075 M sodium barbital buffer, pH 8.5, and 2. 100 μl of a 0.1% suspension (in 0.075 M sodium barbital buffer, pH 8.5) of 0.1 μm europium-imbibed latex beads, poly[styrene-co-(2-chloroethylsulfonylmethyl)styrene-co-2-acrylamido-2-methylpropanesulfonic acid] (88:7:5), to which bovine gamma globulin had been covalently bound (i.e., antigen-coated latex beads), and 3. 10, 5, 2.5, 1.25, 0.63, or 0.31 mg beads (6 μm diameter) to which the gamma globulin fraction of (rabbit) anti-BGG had been adsorbed (i.e., antibody-coated beads), or 4. 10, 5, 2.5, 1.25, 0.63 or 0.31 mg beads to which nonimmune rabbit gamma globulin had been absorbed (i.e. control beads).

The tubes are allowed to stand for one hour after addition of the control or antibody-coated beads. The 6 μm beads settle, and the tubes are observed by UV (365 nm) light for the distribution of latex. In all the control preparations, no red fluorescence due to europium can be observed in the settled beads. A slight film of latex is noticed at the solution-bead interface. In the preparations containing antibody-coated beads, significant fluorescence is noted in the settled bead volume, and diminution of the supernatant fluorescence is apparent when these tubes are compared to those in which comparable amounts of inactive beads were present.

C. Response of the BGG-Coated Fluorescent Latex/Anti-BGGCoated Bead System to BGG Into 1.5 ml snap cap plastic tubes are placed 100 μl of a 10% suspension of the Ab-coated beads described in Part B, 100 μl of the 0.1% antigen-coated latex described in Part B and 100 μl of barbital buffer containing bovine gamma globulin at $10^{-4}$, $5 \times 10^{-5}$, $2.5 \times 10^{-5}$, $1.25 \times 10^{-5}$, $6.25 \times 10^{-6}$, $3.13 \times 10^{-6}$, and 0 M. After incubating at room temperature for one hour, the beads settle and the europium fluorescence in the beads and supernatant can be measured when illuminated by 365 nm light. A regular monotonic increase in supernatant fluorescence and a concomitant diminution of bead fluorescence are noted with increasing concentrations of bovine gamma globulin. The midpoint in this series is between 1.25 and $2.5 \times 10^{-5}$ M bovine gamma globulin (which, when diluted 1:3 in the tube, gives a value of 4.1 to $8.3 \times 10^{-6}$ M).

EXAMPLE 4

Attempt to Load a Polysaccharide Bead With a Europium Chelate

This is a comparative example. A beaded system as described in the earlier-referred-to Leif et al article was prepared as follows:

Two grams of a 10% suspension of AH-Sepharose-4B beads (in saline) were added to two gamma of a 0.5% $Eu^{+3}$ solution in acetone with mixing at 25° C. The solvent was removed at 60° C. No filtration was attempted because the beads would have been removed in this process. A visible settling out occurred within 10 minutes. The beads were then subjected to ultraviolet radiation to detect the presence of fluorescence. None was visible. It was concluded that these beads are not loadable by the method of the present invention.

It has also been observed that though proteins such as antigens may be attached to these surfaces, it was not possible to differentiate precipitation that may have occurred as a result of immunological reaction (i.e., $Ab + Ag \rightarrow AbAg$) from precipitation or settling out of the beads because they are heavy and not dispersible in solution. These beads do not meet the requirement as suitable materials for the subject invention.

The invention has been described in detail with particular reference to certain preferred embodiments thereof, but it will be understood that variations and modifications can be effected within the spirit and scope of the invention.

We claim:

1. A composition comprising protein adsorbed or covalently bound to an aqueous-stabilized fluorescent label comprising a fluorescent rare earth chelate incorporated into a polymeric bead which is derived from a loaded latex wherein said rare earth chelate comprises up to about 7.5 percent by weight of said beads and said loaded latex has a polymeric discontinuous phase which consists essentially of polymer polymerized from one or more ethenic monomers and has an aqueous continuous phase and exhibits essentially no visible coagulation or settling out when 250 ml of the latex containing from about 10 to about 20 weight percent dispersed phase is stirred at 25° C. into an equal volume of acetone over a 1 minute period and subsequently allowed to stand at about 25° C. for 10 minutes.

2. The composition of claim 1 wherein said protein is selected from the group consisting of antibodies, antigens, and enzymes.

3. The composition of claim 1 wherein said protein is selected from the group consisting of antigens and antibodies.

4. The composition of claim 3 wherein the polymeric bead comprises a member selected from the group consisting of poly(n-butyl acrylate-co-styrene-co-2-acrylamido-2-methylpropanesulfonic acid, poly(n-butyl acrylate-co-2-acrylamido-2-methylpropanesulfonic acid, poly[styrene-co-(2-chloroethylsulfonylmethyl)styrene-co-2-acrylamido-2-methylpropanesulfonic acid], poly[styrene-co-acrylamido-co-(2-chloroethylsulfonylmethyl)styrene-co-2-acrylamido-2-methylpropanesulfonic acid], poly(n-butyl acrylate-co-styrene-co-m+p-chloromethylstyrene-co-2-acrylamido-2-methylpropanesulfonic acid, poly[n-butyl acrylate-co-styrene-co-m+p-chloromethylstyrene-co-2-(methacryloyloxy)e- thyltrimethylammonium methosulfate], and poly[styrene-co-acrylamide-co-(2-chloroethylsulfonylmethyl)styrene].

5. The composition of claim 3 wherein the fluorescent rare earth chelate comprises a rare earth and a chelating agent selected from the group consisting of 1,3-diketones; phthalates, naphthalates; dipyridines and terpyridines; p-benzoylbenzoates, p-benzoylacetonates, and phenanthralines.

6. In a method for performing an immunoassay with labeled immunoreagents, the improvement wherein the labeled immunoreagent is an antigen or antibody absorbed or covalently bound to an aqueous-stabilized fluorescent label comprising fluorescent rare earth chelate incorporated into a polymeric bead which is derived from a loaded latex, wherein said rare earth chelate comprises up to about 7.5 percent by weight of said beads and said loaded latex has a polymeric discontinuous phase which consists essentially of polymer polymerized from one or more ethenic monomers and has an aqueous continuous phase and exhibits essentially no visible coagulation or settling out when 250 ml of the latex containing from about 10 to about 20 weight percent dispersed phase is stirred at 25° C. into an equal volume of acetone over a 1 minute period and subsequently allowed to stand at about 25° C. for 10 minutes.

* * * * *